United States Patent [19]

Matsumoto

[11] Patent Number: 5,912,389
[45] Date of Patent: Jun. 15, 1999

[54] STABILIZER AND STABILIZING METHOD FOR AQUEOUS ALIPHATIC ALDEHYDE SOLUTION

[75] Inventor: Shinichi Matsumoto, Kaidsuka, Japan

[73] Assignee: Katayama Chemical, Inc., Osaka, Japan

[21] Appl. No.: 08/949,696

[22] Filed: Oct. 14, 1997

[51] Int. Cl.$^6$ ................................................. C07C 47/00
[52] U.S. Cl. ........................ 568/422; 568/421; 568/449; 568/420
[58] Field of Search .................................. 568/420, 421, 568/422, 449

[56] References Cited

U.S. PATENT DOCUMENTS

| | | | |
|---|---|---|---|
| 4,001,337 | 1/1977 | Diem et al. | 260/606 |
| 4,289,912 | 9/1981 | Harris | 568/422 |
| 4,389,333 | 6/1983 | Werle et al. | 252/40 |

FOREIGN PATENT DOCUMENTS

| | | |
|---|---|---|
| 0066759 | 12/1982 | European Pat. Off. . |
| 52-39008 | 10/1977 | Japan . |
| 57-195463 | 12/1982 | Japan . |
| 57-61009 | 12/1982 | Japan . |
| 58-4741 | 1/1983 | Japan . |
| 62-41593 | 9/1987 | Japan . |
| 4330030 | 11/1992 | Japan . |
| 4330031 | 11/1992 | Japan . |
| 5-29337 | 4/1993 | Japan . |
| 7-69956 | 3/1995 | Japan . |
| 8-2824 | 1/1996 | Japan . |
| 8-2825 | 1/1996 | Japan . |

OTHER PUBLICATIONS

An English Language abstract of South African Patent Application No. 93/0662. Jul. 29, 1994.
English Language Abstract of Japanese Application No. 63303944. Dec. 12, 1988.
English Language Abstract of Japanese Application No. 63307838. Dec. 15, 1988.
English Language Abstract of Japanese Application No. 63112532. May 17, 1988.
English Language Abstract of Japanese Application No. 04330030. Nov. 18, 1992.
English Language Abstract of Japanese Application No. 04330031. Nov. 18, 1992.
English Language Abstract of Japanese Application No. 58004741. Jan. 11, 1983.
English Language Abstract of Japanese Application No. 5239008. Oct. 3, 1977.

*Primary Examiner*—Gary Geist
*Assistant Examiner*—Sreeni Padmanabhan
*Attorney, Agent, or Firm*—Greenblum & Bernstein P.L.C.

[57] ABSTRACT

A stabilizer for an aqueous aliphatic aldehyde solution comprising acetic acid, a halogenated acetic acid or a compound capable of releasing acetic acid or a halogenated acetic acid in water.

14 Claims, No Drawings

STABILIZER AND STABILIZING METHOD FOR AQUEOUS ALIPHATIC ALDEHYDE SOLUTION

BACKGROUND OF THE INVENTION

1. Field of the Invention

The present invention relates to a stabilizer and a stabilizing method for an aqueous aliphatic aldehyde solution. More particularly, the invention relates to a stabilizer and a stabilizing method for preventing turbidity or precipitation in an aqueous aliphatic aldehyde solution in storage.

2. Description of Related Art

Aqueous aliphatic aldehyde solutions tend to generate turbidity or precipitates while they are stored. This nature of the aqueous aliphatic aldehyde solutions makes it very difficult to handle the aqueous aliphatic aldehyde solutions. Formaldehyde, for example, is mostly hydrated in an aqueous solution and exists as an equilibrium mixture of methylene glycol and lower polyoxymethylene glycol. This equilibrium shifts to a higher polymerization as the concentration of formaldehyde increases. A highly polymerized component precipitates as paraformaldehyde which is insoluble in water. This formation of paraformaldehyde results in the turbidity or precipitation of the aqueous formaldehyde solution and, in extreme cases, results in solidification of the whole solution. The aqueous formaldehyde solution is thus poor in stability and very difficult to handle. The turbidity or precipitates cause apparatus and piping of a chemical plant to be blocked. Furthermore, in recent years, a highly concentrated aqueous formaldehyde solution of 50 wt % or more has become industrially used (conventional solutions generally have a concentration of about 37 wt %), and therefore a solution to the above-mentioned problem has eagerly been sought.

In order to prevent the generation of paraformaldehyde during the storage of an aqueous formaldehyde solution, a number of ways have been disclosed in Japanese Patent Publications (Kokoku) Nos. Sho 57(1982)-61009, Sho 62(1987)-41593, Hei 8(1996)-2824 and Hei 8 (1996)-2825 and Japanese Unexamined Patent Publications (Kokai) Nos. Hei 4(1992)-330030 and Hei 4(1992)-330031, in which methanol content in an aqueous formaldehyde solution is increased, storage temperature is raised or various additives are added to the solution.

For another example, glutaraldehyde is a known compound as a purifying agent, disinfectant or sterilant. In order to ensure such effect, an aqueous glutaraldehyde solution must be kept at a weakly alkaline pH of about 7.5 to 8.5. This aqueous glutaraldehyde solution adjusted to the weakly alkaline side also generates turbidity or precipitates when allowed to stand at room temperature or above. Particularly in a medical field, the above-described precipitates enter into gaps of, or adhere to, a surface of medical instruments such as endoscopes and disinfection apparatus for endoscopes, for example. In order to prevent the turbidity and precipitation in the aqueous glutaraldehyde solution, a variety of stabilizers have been disclosed in Japanese Patent Publication (Kokoku) No. Hei 5(1993)-29337 and Japanese Unexamined Patent Publications (Kokai) Nos. Sho 57-195463 and Hei 7(1995)-69956.

The methanol content in the aqueous formaldehyde solution is wished to be decreased in recent years for economic needs, for example, for reducing costs, and for users' needs, for example, for decrease of reaction time in synthesis of resins and for reduction of the burden of disposing of industrial waste water. However, in order to stabilize an aqueous formaldehyde solution containing a reduced amount of methanol., the use amount of a stabilizing agent must be increased and the storage temperature must be raised.

As for the aqueous glutaraldehyde solution, there is a demand for a stabilizer which permits long-term storage in weak alkali.

SUMMARY OF THE INVENTION

The inventors of the present invention have been keenly studying with a view to developing a stabilizer for aqueous aliphatic aldehyde solution which is effective in a small use amount. Finally, the inventors have successfully found a stabilizer which has more excellent stabilizing effect even in a small use amount than the conventional stabilizers. With the stabilizer, the storage temperature does not need to be set high even if the methanol content is low in the case of an aqueous formaldehyde solution. The stabilizing effect of the stabilizer lasts long.

The present invention therefore provides a stabilizer for an aqueous aliphatic aldehyde solution, the stabilizer comprising acetic acid, a halogenated acetic acid or a compound capable of releasing acetic acid or a halogenated acetic acid in water.

In another aspect, the present invention provides a stable aqueous aliphatic aldehyde solution containing an effective amount of the above-described stabilizer.

In still another aspect, the present invention provides a method for stabilizing an aqueous aliphatic aldehyde solution comprising adding an effective amount of the above-described stabilizer to the solution.

DESCRIPTION OF THE PREFERRED EMBODIMENTS

According to the present invention, compounds usable as the stabilizer for an aqueous aliphatic aldehyde solution are acetic acid, halogenated acetic acids and compounds capable of releasing acetic acid or a halogenated acetic acid in water. Here the compounds capable of releasing acetic acid or a halogenated acetic acid in water are those which are gradually hydrolyzed in water to generate acetic acid or a halogenated acetic acid. Examples of halogenated acetic acids include chloroacetic acid and bromoacetic acid, and examples of the compounds capable of generating acetic acid or a halogenated acetic acid in water are acetic anhydride, ethylene glycol diacetate, diethylene glycol diacetate, 1,4-butanediol diacetate, tris(acetoxymethyl)-nitromethane, 2-bromo-2-nitro-1,3-diacetoxypropane, 2,2-dibromo-2-nitro-1-acetoxy-ethane, 1,2-bis(bromoacetoxy) ethane, 1,4-bis(bromoacetoxy)-2-butene, 6-acetoxy-2,4-dimethyl-1,3-dioxane and N-acetoxy-2,2-dibromo-3-nitrilopropionamide.

The use amount of the stabilizer of the invention necessary for preventing the turbidity or precipitation of an aqueous aliphatic aldehyde solution, i.e., effective amount, can be suitably set depending on the concentration, pH, storage temperature and the like of the aqueous aliphatic aldehyde solution. For example, the aqueous formaldehyde solution tends to be more stable as the concentration and pH are lower and the storage temperature is higher. The aqueous glutaraldehyde solution tends to be more stable as the concentration, and pH and the storage temperature are lower. From this fact, when the stability of the aqueous aliphatic aldehyde solution is good, the use amount of the stabilizer may be reduced. The use amount of the stabilizer may generally be 0.0001 to 0.1 mol, preferably 0.001 to 0.01 mol, to one mol of the aliphatic aldehyde. Where the stabilizer is used within the above use amount range, the stabilizer is easily dissolved in the aqueous aliphatic aldehyde solution and also can exert a sufficient stabilizing effect.

Examples of the aqueous aliphatic aldehyde solutions with which the stabilizer of the present invention is used include an aqueous solution of formaldehyde, acetaldehyde, glutaraldehyde, propionaldehyde or glyoxaladehyde. In the case of an aqueous formaldehyde solution, in particular, methylal, methanol, dimethyl ether, formic acid, methyl formate and trioxane may be contained depending on a source, a preparation process and the like of formaldehyde.

The concentration of the aliphatic aldehyde in aqueous solution is not particularly limited, but is usually less than 60 wt %.

EXAMPLES

The present invention is explained in detail by way of the following preparation examples and experiments. Part(s) stands for part(s) by weight hereinafter. A value in parentheses for each stabilizer indicates the number of moles of the stabilizer with respect to one mol of an aliphatic aldehyde.

Preparation Example 1

| | |
|---|---|
| 50 wt % aqueous formaldehyde solution | 99.9 parts |
| Acetic acid | 0.1 part |
| | (0.001) |

Preparation Example 2

| | |
|---|---|
| 50 wt % aqueous formaldehyde solution | 99.9 parts |
| Acetic anhydride | 0.1 part |
| | (0.00059) |

Preparation Example 3

| | |
|---|---|
| 50 wt % aqueous formaldehyde solution | 99.9 parts |
| Ethylene glycol diacetate | 0.1 part |
| | (0.00041) |

Preparation Example 4

| | |
|---|---|
| 50 wt % aqueous formaldehyde solution | 99.9 parts |
| Diethylene glycol diacetate | 0.1 part |
| | (0.00032) |

Preparation Example 5

| | |
|---|---|
| 50 wt % aqueous formaldehyde solution | 99.9 parts |
| 1,4-butanediol diacetate | 0.1 part |
| | (0.00035) |

Preparation Example 6

| | |
|---|---|
| 50 wt % aqueous formaldehyde solution | 99.9 parts |
| Tris(acetoxymethyl)nitromethane | 0.1 part |
| | (0.00022) |

Preparation Example 7

| | |
|---|---|
| 50 wt % aqueous formaldehyde solution | 99.9 parts |
| 2-bromo-2-nitro-1,3-diacetoxypropane | 0.1 part |
| | (0.00021) |

Preparation Example 8

| | |
|---|---|
| 50 wt % aqueous formaldehyde solution | 99.9 parts |
| 2,2-dibromo-2-nitro-1-acetoxyethane | 0.1 part |
| | (0.00028) |

Preparation Example 9

| | |
|---|---|
| 50 wt % aqueous formaldehyde solution | 99.9 parts |
| 1,2-bis(bromoacetoxy)ethane | 0.1 part |
| | (0.00027) |

Preparation Example 10

| | |
|---|---|
| 50 wt % aqueous formaldehyde solution | 99.9 parts |
| 1,4-bis(bromoacetoxy)-2-butene | 0.1 part |
| | (0.00024) |

Preparation Example 11

| | |
|---|---|
| 50 wt % aqueous formaldehyde solution | 99.9 parts |
| 6-acetoxy-2,4-dimethyl-1,3-dioxane | 0.1 part |
| | (0.00035) |

Preparation Example 12

| | |
|---|---|
| 50 wt % aqueous formaldehyde solution | 99.9 parts |
| N-acetoxy-2,2-dibromo-3-nitrilopropionamide | 0.1 part |
| | (0.00027) |

Preparation Example 13

| | |
|---|---|
| 50 wt % aqueous formaldehyde solution | 98.9 parts |
| Acetic acid | 0.1 part |
| | (0.001) |
| Methanol | 1.0 part |

Preparation Example 14

| | |
|---|---|
| 50 wt % aqueous formaldehyde solution | 98.9 parts |
| Acetic anhydride | 0.1 part |
| | (0.00059) |
| Methanol | 1.0 part |

Preparation Example 15

| | |
|---|---|
| 50 wt % aqueous formaldehyde solution | 98.9 parts |
| Ethylene glycol diacetate | 0.1 part |
| | (0.00042) |
| Methanol | 1.0 part |

Preparation Example 16

| | |
|---|---|
| 50 wt % aqueous formaldehyde solution | 98.9 parts |
| Diethylene glycol diacetate | 0.1 part |
| | (0.00032) |
| Methanol | 1.0 part |

Preparation Example 17

| | |
|---|---|
| 50 wt % aqueous formaldehyde solution | 98.9 parts |
| 1,4-butanediol diacetate | 0.1 part |
| | (0.00035) |
| Methanol | 1.0 part |

Preparation Example 18

| | |
|---|---|
| 50 wt % aqueous formaldehyde solution | 98.9 parts |
| Tris(acetoxymethyl)nitromethane | 0.1 part |
| | (0.00022) |
| Methanol | 1.0 part |

Preparation Example 19

| | |
|---|---|
| 50 wt % aqueous formaldehyde solution | 98.9 parts |
| 2-bromo-2-nitro-1,3-diacetoxypropane | 0.1 part |
| | (0.00021) |
| Methanol | 1.0 part |

Preparation Example 20

| | |
|---|---|
| 50 wt % aqueous formaldehyde solution | 98.9 parts |
| 2,2-dibromo-2-nitro-1-acetoxyethane | 0.1 part |
| | (0.00029) |
| Methanol | 1.0 part |

Preparation Example 21

| | |
|---|---|
| 50 wt % aqueous formaldehyde solution | 98.9 parts |
| 1,2-bis(bromoacetoxy)ethane | 0.1 part |
| | (0.00027) |
| Methanol | 1.0 part |

Preparation Example 22

| | |
|---|---|
| 50 wt % aqueous formaldehyde solution | 98.9 parts |
| 1,4-bis(bromoacetoxy)-2-butene | 0.1 part |
| | (0.00024) |
| Methanol | 1.0 part |

Preparation Example 23

| | |
|---|---|
| 50 wt % aqueous formaldehyde solution | 98.9 parts |
| 6-acetoxy-2,4-dimethyl-1,3-dioxane | 0.1 part |
| | (0.00035) |
| Methanol | 1.0 part |

Preparation Example 24

| | |
|---|---|
| 50 wt % aqueous formaldehyde solution | 98.9 parts |

-continued

| N-acetoxy-2,2-dibromo-3-nitrilopropionamide | 0.1 part (0.00028) |
| --- | --- |
| Methanol | 1.0 part |

Comparative Preparation Example 1

| 50 wt % aqueous formaldehyde solution | 99 parts |
| --- | --- |
| Methanol | 1 part |

Comparative Preparation Example 2

| 50 wt % aqueous formaldehyde solution | 95 parts |
| --- | --- |
| Methanol | 5 parts |

Comparative Preparation Example 3

| 50 wt % aqueous formaldehyde solution | 98.9 parts |
| --- | --- |
| Acetylacetone | 0.1 part |
| Methanol | 1.0 part |

Experiment 1 (Stability Test on 50 wt % aqueous formaldehyde solution at 50° C.)

Aqueous formaldehyde solutions prepared in Preparation Examples 1 to 24 and Comparative Preparation Examples 1 to 3 were tested on stability at 50° C. with days. Evaluation was made according to the following criteria:

◯: No precipitates were observed in an aqueous formaldehyde solution.

Δ: An aqueous formaldehyde solution became slightly white opaque.

X: Precipitates were generated in an aqueous formaldehyde solution.

The results are shown in Table 1

TABLE 1

| | Stability of aqueous solution | | | |
| --- | --- | --- | --- | --- |
| Preparation | after 1 day | after 3 days | after 7 days | after 14 days |
| Example 1 | ◯ | ◯ | Δ | Δ |
| Example 2 | ◯ | ◯ | ◯ | Δ |
| Example 3 | ◯ | ◯ | ◯ | Δ |
| Example 4 | ◯ | ◯ | ◯ | Δ |
| Example 5 | ◯ | ◯ | ◯ | Δ |
| Example 6 | ◯ | ◯ | ◯ | ◯ |
| Example 7 | ◯ | ◯ | ◯ | ◯ |
| Example 8 | ◯ | ◯ | ◯ | ◯ |
| Example 9 | ◯ | ◯ | ◯ | ◯ |
| Example 10 | ◯ | ◯ | ◯ | ◯ |
| Example 11 | ◯ | ◯ | ◯ | ◯ |
| Example 12 | ◯ | ◯ | ◯ | ◯ |
| Example 13 | ◯ | ◯ | ◯ | ◯ |
| Example 14 | ◯ | ◯ | ◯ | ◯ |
| Example 15 | ◯ | ◯ | ◯ | ◯ |
| Example 16 | ◯ | ◯ | ◯ | ◯ |
| Example 17 | ◯ | ◯ | ◯ | ◯ |
| Example 18 | ◯ | ◯ | ◯ | ◯ |
| Example 19 | ◯ | ◯ | ◯ | ◯ |
| Example 20 | ◯ | ◯ | ◯ | ◯ |
| Example 21 | ◯ | ◯ | ◯ | ◯ |
| Example 22 | ◯ | ◯ | ◯ | ◯ |
| Example 23 | ◯ | ◯ | ◯ | ◯ |
| Example 24 | ◯ | ◯ | ◯ | ◯ |
| Comparative Example 1 | Δ | X | X | X |
| Comparative Example 2 | X | X | X | X |
| Comparative Example 3 | X | X | X | X |

Table 1 shows that the stabilizers of the present invention have stabilizing effect.

Experiment 2 (Stability Test on 37 wt % aqueous formaldehyde solution at 20° C.)

Each stabilizer shown in Table 2, 0.1 wt %, was added to a 37wt % aqueous formaldehyde solution. The solutions were allowed to stand at 20° C. for 7 days, and then the appearance of the solutions was observed. Evaluation was made according to the same criteria as described in Experiment 1. The results are shown in Table 2, wherein a value in parentheses for each stabilizer indicates the number of moles of the stabilizer with respect to one mol of the aliphatic aldehyde.

TABLE 2

| | Stabilizer | Evaluation |
| --- | --- | --- |
| Examples | 2-bromo-2-nitro-1,3-diacetoxypropane (0.00029) | ◯ |
| | 2,2-dibromo-2-nitro-1-acetoxyethane (0.00038) | ◯ |
| | 1,2-bis(bromoacetoxy)ethane (0.00036) | ◯ |
| | 1,4-bis(bromoacetoxy)-2-butene (0.00032) | ◯ |
| | 6-acetoxy-2,4-dimethyl-1,3-dioxane (0.00047) | ◯ |
| Comparative Examples | Acetylacetone (0.00081) | X |
| | No stabilizer added | X |

Table 2 shows that the stabilizers of the present invention also have stabilizing effect on aqueous formaldehyde solutions of different concentrations.

Experiment 3 (Stability Test on 20 wt % aqueous formaldehyde solution at 5° C.)

Each stabilizer shown in Table 3, 0.1 wt %, and methanol, 1 wt %, were added to a 20wt % aqueous formaldehyde solution. The solutions were allowed to stand at 5° C. for 14 days, and then the appearance of the solutions was observed. Evaluation was made according to the same criteria as described in Experiment 1. The results are shown in Table 3, wherein a value in parentheses for each stabilizer indicates the number of moles of the stabilizer with respect to one mol of the aliphatic aldehyde.

TABLE 3

| | Stabilizer | Evaluation |
| --- | --- | --- |
| Examples | 2-bromo-2-nitro-1,3-diacetoxypropane (0.00053) | ◯ |
| | 2,2-dibromo-2-nitro-1-acetoxyethane (0.00072) | ◯ |
| | 1,2-bis(bromoacetoxy)ethane (0.00068) | ◯ |
| Comparative Examples | Methanol | X |
| | No stabilizer added | X |

Table 3 shows that the stabilizers of the present invention have stabilizing effect on an aqueous formaldehyde solution containing a small amount of methanol.

Experiment 4 (Stability test on 50 wt % aqueous glutaraldehyde solution at 50° C.)

Each stabilizer shown in Table 4, 0.1 wt %, was added to a 50wt % aqueous glutaraldehyde solution adjusted to pH 6.0 with sodium hydroxide. The solutions were allowed to stand at 50° C. for 30 days, and then the appearance of the solutions was observed. Evaluation was made according to the same criteria as described in Experiment 1. The results are shown in Table 4, wherein a value in parentheses for each stabilizer indicates the number of moles of the stabilizer with respect to one mol of the aliphatic aldehyde.

TABLE 4

| | Stabilizer | Evaluation |
|---|---|---|
| Examples | Ethylene glycol diacetate (0.00137) | ○ |
| | 2-bromo-2-nitro-1,3-diacetoxypropane (0.00070) | ○ |
| | 2,2-dibromo-2-nitro-1-acetoxyethane (0.00095) | ○ |
| | 1,2-bis(bromoacetoxy)ethane (0.00089) | ○ |
| | 6-acetoxy-2,4-dimethyl-1,3-dioxane (0.00115) | ○ |
| | N-acetoxy-2,2-dibromo-3-nitrilopropionamide (0.00091) | ○ |
| Comparative Examples | Acetylacetone (0.002) | X |
| | No stabilizer added | X |

Table 4 shows that the stabilizers of the present invention have stabilizing effect on aqueous solutions of different aldehydes.

Experiment 5 (Stability test on aqueous formaldehyde solutions with varying the concentration, pH and temperature)

Paraformaldehyde and water were mixed with stirring at 80° C. to obtain aqueous formaldehyde solutions of different concentrations. The obtained solutions were adjusted to various pH by adding a small amount of sodium hydroxide or hydrochloric acid. The solutions were then cooled to various temperatures to obtain samples to be tested.

A stabilizer shown in Table 5 was added to the obtained samples in concentrations in Table 5. The number of days was counted until precipitates were generated in the solutions or the solutions became white opaque. The results are shown in Table 5, wherein a value in parentheses for each stabilizer indicates the number of moles of the stabilizer with respect to one mol of the aliphatic aldehyde.

TABLE 5

| Concentration of formaldehyde (wt %) | pH | Temperature (° C.) | Concentration of 1,4-butanediol diacetate (mg/l) | Days until precipitation or turbidity was generated (days) |
|---|---|---|---|---|
| 30 | 5.5 | 5 | 0 | 1 |
| | | | 100 (0.00006) | 3 |
| | | | 300 (0.00017) | 10 |
| | | | 500 (0.00029) | 22 |
| | | | 1000 (0.00057) | >30 |
| | 5.6 | 30 | 0 | 5 |
| | | | 250 (0.00014) | >30 |
| | | | 500 (0.00029) | >30 |
| | | | 1000 (0.00057) | >30 |
| 40 | 5.4 | 30 | 0 | 1 |
| | | | 250 (0.00011) | 19 |
| | | | 500 (0.00022) | >30 |
| | | | 1000 (0.00043) | >30 |
| 50 | 2.0 | 40 | 0 | 1 |
| | | | 500 (0.00017) | >30 |
| | | | 1000 (0.00034) | >30 |
| | 5.8 | | 0 | 1 |
| | | | 500 (0.00017) | 15 |
| | | | 1000 (0.00034) | >30 |
| | | 50 | 0 | 1 |
| | | | 500 (0.00017) | >30 |
| | | | 1000 (0.00034) | >30 |

Table 5 shows that as the concentration and pH of the aqueous formaldehyde solution are lower and the temperature of the solution is higher, the solution tends to be more stable and can be stabilized well even with a small amount of the stabilizer.

Experiment 6 (Stability test on aqueous glutaraldehyde solutions with varying the concentration, pH and temperature)

A 50 wt % aqueous glutaraldehyde solution (produced by Daicel Chemical Industries, Ltd., Japan) was diluted with tap water to have different concentrations. The obtained solutions were adjusted to various pH by adding a small amount of sodium hydroxide.

A stabilizer shown in Table 6 was added to each of the obtained solutions with varying the concentration. The number of days until precipitates were generated in the solutions or the solutions became white opaque was counted under different conditions. The results are shown in Table 6, wherein a value in parentheses for each stabilizer indicates the number of moles of the stabilizer with respect to one mol of the aliphatic aldehyde.

TABLE 6

| Concentration of glutaraldehyde (wt %) | pH | Temperature (° C.) | Concentration of ethylene glycol diacetate (mg/l) | Days until precipitation or turbidity was generated (days) |
|---|---|---|---|---|
| 50 | 8 | 50 | 0 | 1 |
| | | | 1000 (0.00137) | 2 |
| | 7 | | 0 | 1 |
| | | | 1000 (0.00137) | 4 |
| | 6 | | 0 | 1 |
| | | | 1000 (0.00137) | >30 |
| 10 | 8 | | 0 | 3 |
| | | | 200 (0.00137) | 5 |
| | | | 1000 (0.00685) | >30 |
| | 7 | | 0 | 6 |
| | | | 200 (0.00137) | 10 |
| | | | 1000 (0.00685) | >30 |
| | 6 | | 0 | 11 |
| | | | 200 (0.00137) | >30 |
| | | | 1000 (0.00685) | >30 |
| | 8 | 40 | 0 | 8 |
| | | | 200 (0.00137) | 16 |
| | | | 1000 (0.00685) | >30 |
| 2 | 8 | 50 | 0 | 4 |
| | | | 40 (0.00137) | 8 |
| | | | 200 (0.00685) | >30 |
| | 7 | | 0 | 7 |
| | | | 40 (0.00137) | 15 |
| | | | 200 (0.00685) | >30 |

Table 6 shows that as the concentration, pH and temperature of the aqueous glutaraldehyde solution are lower, the solution tends to be more stable and can be stabilized well even with a small amount of the stabilizer.

According to the present invention, acetic acid, a halogenated acetic acid or a compound capable of releasing acetic acid or a halogenated acetic acid in water is added in an effective amount as a stabilizer to an aqueous solution of an aliphatic aldehyde such as formaldehyde, acetaldehyde, glutaraldehyde, propionaldehyde or glyoxal. The stabilizer, even in a small use amount, has an effect of greatly inhibiting the turbidity or precipitation of the aqueous aliphatic aldehyde solution and therefore an excellent stabilizing effect can be obtained. This effect is more excellent than the effects of the conventional stabilizers. Specially, the stabilizer of the present invention can provide lasting stability regardless of storage temperature.

What is claimed is:

1. A composition comprising a combination of a stable aqueous aliphatic aldehyde solution and an effective amount of a stabilizer comprising, a halogenated acetic acid or a compound capable of releasing acetic acid or a halogenated acetic acid in water.

2. A stable aqueous aldehyde solution according to claim 1, wherein the halogenated acetic acid comprises a member selected from the group consisting of chloroacetic acid and bromoacetic acid.

3. A stable aqueous aliphatic aldehyde solution according to claim 1, wherein the compound capable of releasing acetic acid or a halogenated acetic acid in water comprises at least one compound selected from the group consisting of acetic anhydride, ethylene glycol diacetate, diethylene glycol diacetate, 1,4-butanediol diacetate, tris(acetoxymethyl)-nitromethane, 2-bromo-2-nitro-1,3-diacetoxypropane, 2,2-dibromo-2-nitro-l-acetoxyethane, 1,2-bis(bromoacetoxy)ethane, 1,4-bis(bromoacetoxy)-2-butene, 6-acetoxy-2,4-dimethyl-1,3-dioxane and N-acetoxy-2,2-dibromo-3-nitrilopropionamide.

4. A stable aqueous aliphatic aldehyde solution according to claim 1, wherein the aqueous aliphatic aldehyde solution is an aqueous solution comprising a member selected from the group consisting of formaldehyde, acetaldehyde, glutaraladehyde, propionaldehyde or glyoxaldehyde.

5. A stable aqueous aldehyde solution according to claim 1, wherein the aqueous aliphatic aldehyde solution is an aqueous solution comprising a member selected from the group consisting of formaldehyde and glutaraldehyde having a concentration of 20 to 50wt %.

6. A stable aqueous aliphatic aldehyde solution according to claim 1, wherein the effective amount of the stabilizer is 0.0001 to 0.1 mol to one mol of the aliphatic aldehyde.

7. A stable aqueous aliphatic aldehyde solution according to claim 6, wherein the effective amount of the stabilizer is 0.001 to 0.1 mol to one mol of the aliphatic aldehyde.

8. A method of stabilizing an aqueous aliphatic aldehyde solution comprising adding an effective amount of a stabilizer for an aqueous aliphatic aldehyde solution comprising a halogenated acetic acid or a compound capable of releasing acetic acid or a halogenated acetic acid in water.

9. A method of stabilizing an aqueous aliphatic aldehyde solution according to claim 8, wherein the halogenated acetic acid comprises a member selected from the group consisting of chloroacetic acid and bromoacetic acid.

10. A method of stabilizing an aqueous aliphatic aldehyde solution according to claim 8, wherein the compound capable of releasing acetic acid or a halogenated acetic acid in water comprises at least one compound selected from the group consisting of acetic anhydride, ethylene glycol diacetate, diethylene glycol diacetate, 1,4-butanediol diacetate, tris(acetoxymethyl)-nitromethane, 2-bromo-2-nitro-1,3-diacetoxypropane, 2,2-dibromo-2-nitro-1-acetoxyethane, 1,2-bis(bromoacetoxy)ethane, 1,4-bis(bromoacetoxy)-2-butene, 6-acetoxy-2,4-dimethyl-1,3-dioxane and N-acetoxy-2,2-dibromo-3-nitrilopropionamide.

11. A method of stabilizing an aqueous aliphatic aldehyde solution according to claim 8, wherein the aqueous aliphatic aldehyde solution is an aqueous solution comprising a member selected from the group consisting of formaldehyde, acetaldehyde, glutaraladehyde, propionaldehyde or glyoxaldehyde.

12. A method of stabilizing an aqueous aldehyde solution according to claim 8, wherein the aqueous aliphatic aldehyde solution is an aqueous solution comprising a member selected from the group consisting of formaldehyde and glutaraldehyde having a concentration of 20 to 50wt %.

13. A method of stabilizing an aqueous aliphatic aldehyde solution according to claim 8, wherein the effective amount of the stabilizer is 0. 0001 to 0. 1 mol to one mol of the aliphatic aldehyde.

14. A method of stabilizing an aqueous aliphatic aldehyde solution according to claim 13, wherein the effective amount of the stabilizer is 0.001 to 0.1 mol to one mol of the aliphatic aldehyde.

* * * * *